United States Patent [19]

Heurtaux

[11] Patent Number: 5,173,114
[45] Date of Patent: Dec. 22, 1992

[54] BASAL CERAMIC LAYER - RECONSTRUCTION

[75] Inventor: Michel Heurtaux, Romorantin, France

[73] Assignee: Suissor, S.A., Angers, France

[21] Appl. No.: 827,497

[22] Filed: Jan. 30, 1992

Related U.S. Application Data

[63] Continuation of Ser. No. 590,324, Jun. 20, 1990, abandoned, which is a continuation of Ser. No. 346,298, May 1, 1989, abandoned, which is a continuation of Ser. No. 226,560, Jul. 18, 1988, abandoned, which is a continuation of Ser. No. 910,847, Sep. 24, 1986, abandoned, which is a continuation of Ser. No. 699,987, Feb. 11, 1985, abandoned.

[30] Foreign Application Priority Data

Feb. 15, 1984 [FR] France ................. 84 02295

[51] Int. Cl.$^5$ ................. A61C 13/083; C03C 8/02
[52] U.S. Cl. ................. 106/35; 433/212.1; 433/208; 501/18; 501/21; 501/67
[58] Field of Search ................. 501/16, 17, 18, 21, 501/67; 106/35; 433/208, 212.1, 222.1, 201.1

[56] References Cited

U.S. PATENT DOCUMENTS

| | | | |
|---|---|---|---|
| 3,383,344 | 5/1968 | Gill | 501/20 X |
| 4,196,004 | 4/1980 | Berretz | 501/17 |
| 4,215,033 | 7/1980 | Bowen | 260/42.15 |
| 4,437,192 | 3/1984 | Fujiu et al. | 501/18 |

FOREIGN PATENT DOCUMENTS

| | | |
|---|---|---|
| 1441336 | 4/1971 | Fed. Rep. of Germany . |
| 1378540 | 12/1963 | France . |
| 0013590 | 2/1978 | Japan ................. 433/222 |

OTHER PUBLICATIONS

Chemical Abstracts, vol. 89, No. 22, Nov. 27, 1978, Ref. No. 186102a, p. 377.

*Primary Examiner*—Karl Group
*Attorney, Agent, or Firm*—Jones, Tullar & Cooper

[57] ABSTRACT

The present invention relates to a ceramic basal layer for opacifying the metal coping of a ceramo-metallic dental reconstruction.

The ceramic basal layer for opacifying the metal coping of a ceramo-metallic dental reconstruction consists of an undercoat of opaque slip produced from a glass frit high in fluxes and in particular in $B_2O_3$, covered with an opaque layer produced from a glass frit high in opacifying metal oxides and containing approximately 30% by weight of refractory particles with a particle size of between approximately 40 microns and approximately 100 microns.

1 Claim, No Drawings

BASAL CERAMIC LAYER - RECONSTRUCTION

This is a continuation of co-pending application Ser. No. 07/590,324 filed on Jun. 20, 1990, now abandoned, which is a continuation of Ser. No. 07/346,298, filed May 1, 1989, now abandoned, which is a continuation of 07/226,560, filed Jul. 18, 1988, now abandoned, which is a continuation of 06/910,847, filed Sep. 24, 1986, now abandoned, which is a continuation of 06/699,987, filed Feb. 11, 1985, now abandoned.

The present invention relates to the technical field of ceramo-metallic dental reconstructions. It relates more particularly to the composition of ceramic glass employed to produce various types of dental reconstruction, such as crowns, inlays, bridges, and the like.

Dental reconstructions of this type are usually produced from a series of ceramic layers covering a metal coping, for example laid on the stump of a tooth reduced after shaping with the drill. This series of ceramic layers consists of a basal opacifying layer, two intermediate layers known under the terms of "dentine" and "incisal", and a transparent surface layer intended to resemble the gleam of the enamel of the natural tooth.

The subject of the present invention is aimed more especially at the basal ceramic layer for opacifying the metal coping of such a dental reconstruction.

As its name indicates, such a layer is mainly intended to hide the metallic appearance of the supporting coping. It is therefore essential to give it good opacifying properties. However, this is not enough. In fact, to obtain good mechanical strength and good fracture toughness of the prosthesis, it is essential to ensure perfect bonding of the opaque ceramic layer to the metal coping. The various solutions proposed hitherto do not produce a satisfactory adhesion in practice.

The aim of the present invention was precisely to develop an opaque dental ceramic which, in addition to its improved adhesive properties, is endowed with an outstanding opacifying power. This layer according to the invention moreover has, after being baked, a rough surface quality responsible for good light scatter, which makes it possible to avoid any unpleasant reflection effect of the prosthesis which, for this reason, would not truly restore the appearance of the natural tooth.

It should be noted, moreover, that, as a result of the better opacifying power, the dental ceramic according to the invention can be applied as a thinner layer, which leaves more space available for applying the following coats, which thus become easier to mold by the prosthetist.

Furthermore, the opaque dental ceramic composition according to the invention has been adapted to conform in expansion with its adjacent layers, and in particular with its metal support. This compatibility is further considerably facilitated by its better opacity, which permits it to be deposited as a thinner layer.

The present invention which makes it possible to reconcile, on the one hand, the adhesion and, on the other hand, the opacity of this type of ceramic layer, springs from the parent concept based on separating into two distinct layers the single opaque layer usually employed in the prior art. The first undercoat, called "opaque slip", in direct contact with the reinforcement, is intended to contribute good adhesion to the metal, while the other layer, referred to as "opaque", has been designed to contribute the sufficient degree of opacity.

In accordance with the present invention, the basal ceramic layer for opacifying the metal coping of a ceramo-metallic dental reconstruction consists of an undercoat of opaque slip obtaind from a glass frit high in fluxes and in particular in $B_2O_3$, covered with an opaque layer obtained from a glass frit high in opacifying metal oxides and containing approximately 30% by weight of refractory particles with a particle size of between approximately 40 microns and approximately 100 microns.

Other features and advantages of the present invention will become apparent from the reading of the detailed description which follows, relying particularly on individual examples of application, which are given simply as illustrations.

The glass frit which is high in fluxes and intended to form the undercoat of opaque slip in contact with the metal coping, advantageously contains approximately 8 to approximately 14% by weight, and preferably from approximately 9 to approximately 11% by weight, of $B_2O_3$. It is precisely this high content of boron oxide which makes it possible to improve the metal adhesion capacity of this undercoat of opaque slip. It should be noted, however, that $B_2O_3$ contents above approximately 14% by weight would result in glass frits which cannot be used in practice, since they would become too readily melted. In fact, an undercoat of opaque slip must not have melting temperatures which are too low, since its melting temperature must in any event remain above those of the following top layers which are laid down and subsequently heat-stabilized.

Insofar as the opaque layer as such is concerned, this of course contains opacifying agents such as tin oxide, titanium oxide and zirconium oxide, in a high concentration. However, the opacifying capacity of this layer is considerably increased by the presence of a high proportion (of the order of 30% by weight) of relatively large refractory particles, that is to say with a particle size of between approximately 40 and approximately 100 microns. The presence of these refractory particles of relatively large sizes produces, after baking, a roughness in the surface of this opaque layer which contributes an effect of light scatter through the more translucent upper layers and thus improves the effect of tooth "depth".

Two examples of composition of glass frits intended for producing an undercoat of opaque slip and an opaque layer are given below by way of illustration.

EXAMPLE OF OVERALL COMPOSITION OF OPAQUE SLIP

A glass frit of this type, which is high in fluxes and has produced satisfactory results in practice, corresponds, for example, to the following composition:

| | |
|---|---|
| $SiO_2$ | 46 to 48% by weight |
| $Al_2O_3$ | 10 to 12% by weight |
| CaO | 1 to 1.5% by weight |
| MgO | 0.5 to 1.5% by weight |
| $K_2O$ | 10 to 11% by weight |
| $Na_2O$ | 6 to 9% by weight |
| $B_2O_3$ | 9 to 11% by weight |
| $ZrO_2$ | 1.5 to 2% by weight |
| $SnO_2$ | 6 to 8% by weight |
| $TiO_2$ | 0.5 to 1% by weight. |

Preferably, such a glass frit has an average particle size of approximately 12 microns.

EXAMPLE OF OVERALL COMPOSITION OF OPAQUE LAYER

A glass frit high in opacifying metal oxides, which is employed in a satisfactory manner in practice to produce an opaque layer according to the invention, corresponds, for example, to the following overall composition:

| | | |
|---|---|---|
| $SiO_2$ | 42 to 46% | by weight |
| $Al_2O_3$ | 14 to 18% | by weight |
| $CaO$ | 0.8 to 1.7% | by weight |
| $MgO$ | 0.5 to 1.5% | by weight |
| $K_2O$ | 11 to 13% | by weight |
| $Na_2O$ | 3 to 6% | by weight |
| $B_2O_3$ | 5 to 8% | by weight |
| $ZrO_2$ | 3 to 5% | by weight |
| $SnO_2$ | 11 to 14% | by weight |
| $TiO_2$ | 0.5 to 3% | by weight. |

The above glass frit high in opacifying metal oxides advantageously has a mean particle size which is slightly greater, for example approximately 36 microns, while retaining the presence of a fraction of the order of 30% by weight of particles ranging from approximately 40 to approximately 100 microns, favoring the refractory particles. This refractory particle fraction contains a proportion of opacifying metal oxides which is always greater than 25% by weight, that is to say that these particles have a higher content of opacifying agents than the remainder of the composition.

The glass frits required for producing the layers according to the present invention are prepared in a conventional manner, from powdered mixtures of the required components such as determined earlier. Such a powdered mixture is, for example, heated for one hour at a temperature of the order of 1500° C., which, on melting, produces a homogenization, followed, for example, by quenching to produce the frit which can subsequently be subjected to a grinding or granulation operation.

This grinding operation is carried out in a controlled manner to obtain the particle sizes required in accordance with the present invention.

The present application also relates to glass frits required for producing the ceramic layers called "opaque slip" or "opaque", which are distinguished by a composition containing:
10 to 30% by weight of active products,
60 to 80% by weight of a propellant gas,
10 to 30% by weight of a solvent with a vaporization temperature of between approximately 40 and approximately 80° C., and
4 to 6% by weight of a glue.

The propellant gas may consist, for example, of one or more chlorofluorinated hydrocarbons (Freon®). The mixture of glue and solvent may consist, for example of officinal collodion dissolved in ethyl acetate. The solvent may advantageously also consist of a chlorinated hydrocarbon, for example $CH_2Cl_2$, and the glue may also consist of an acrylic or, preferably, cyanoacrylic, glue.

A composition of this kind is thus suitable for being packaged in a dispenser bottle of the aerosol type.

This glass frit composition may thus be presented as such, to be ready for direct use. Simple spraying on the metal coping with the aid of an aerosol can thus makes it possible to produce thin layers of opaque slip or of opaque composition.

These layers are then fixed in a conventional manner by baking, for example in the course of a heat treatment at a temperature of the order of 800° to 850° C. for 7 to 8 minutes. It should also be noted that as a result of the particular compositions of the ceramics which are the subject of the present invention, it is thus possible to lower fairly substantially the baking temperature for fixing these layers. In fact, in the prior art such a baking temperature was never lower than approximately 950° C. Moreover, the combination of the basal layer consisting of the layer of opaque slip and of the opaque layer may be applied so as to produce a layer with a mean thickness of approximately 80 microns. In the conventional prior art involving application with a brush, it was impossible, strictly speaking, to attain thicknesses below approximately 120 microns.

The heat treatment for fixing the layer of opaque slip and the opaque layer generally requires two successive bakings. However, when the glass frits required to produce the opaque slip and opaque layers are deposited with the aid of an aerosol composition containing, for example, a cyanoacrylic glue, it is possible to fix the combination of the opaque layers and of the successive layers during the same baking. Immediately after the spraying, the propellant gas and the solvents disappear rapidly and the glue acts as a fixer for the layers on the reinforcement. The solvent or the plasticizer sprayed when the successive layers, of dentine, incisal and transparent compositions, are deposited is chosen such that it does not dissolve a glue of this type. Consequently, the basal layers are not affected by the deposition of the following layers, and it is thus possible to fix all the ceramic layers during a single baking, which represents a considerable saving in time. It should also be noted that the lowest temperatures for baking the basal layers are thus brought close to those of the other layers and, in fact, make it possible to envisage a single baking of the whole of the ceramo-metallic prosthesis.

Naturally, the present invention is not restricted in any way to the examples of embodiment described above, but it is perfectly possible, without departing from the scope of the present invention thereby, to envisage a number of alternative embodiments thereof.

I claim:

1. In a ceramo-metallic dental reconstruction applied to a tooth stump, including: a basal ceramic opacifying layer adhered to the tooth stump; a dentine intermediate layer adhered to the basal ceramic opacifying layer and an incisal intermediate layer adhered to the dentine intermediate layer; and a transparent surface layer, the improvement wherein the basal ceramic opacifying layer comprises:
  an undercoat of opaque slip produced from a first glass frit having a mean particle size of about 12 μm; and
  an opaque layer covering the undercoat of opaque slip produced from a second glass frit having a mean particle size of about 30 μm, and containing additionally 30% by weight of refractory particles having a particle size ranging from about 40 μm to about 100 μm, wherein the first glass frit corresponds to the following composition:

| | |
|---|---|
| $SiO_2$ | 46 to 48% by weight; |
| $Al_2O_3$ | 10 to 12% by weight; |

| | |
|---|---|
| CaO | 1 to 1.5% by weight; |
| MgO | 0.5 to 1.5% by weight; |
| $K_2O$ | 10 to 11% by weight; |
| $Na_2O$ | 6 to 9% by weight; |
| $B_2O_3$ | 9 to 11% by weight; |
| $ZrO_2$ | 1.5 to 2% by weight; |
| $SnO_2$ | 6 to 8% by weight; and |
| $TiO_2$ | 0.5 to 1% by weight, | and the second glass frit corresponds to the following composition:

| | |
|---|---|
| $SiO_2$ | 42 to 46% by weight; |
| $Al_2O_3$ | 14 to 18% by weight; |
| CaO | 0.8 to 1.7% by weight; |
| MgO | 0.5 to 1.5% by weight; |
| $K_2O$ | 11 to 13% by weight; |
| $Na_2O$ | 3 to 6% by weight; |
| $B_2O_3$ | 5 to 8% by weight; |
| $ZrO_2$ | 3 to 5% by weight; |
| $SnO_2$ | 11 to 14% by weight; and |
| $TiO_2$ | 0.5 to 3% by weight. |

* * * * *